United States Patent [19]

Sih

[11] 4,267,352
[45] May 12, 1981

[54] 19-HYDROXY-19-METHYL-6-OXO-PGF$_1$ SULFONYLAMIDES

[75] Inventor: John C. Sih, Portage, Mich.

[73] Assignee: The Upjohn Company, Kalamazoo, Mich.

[21] Appl. No.: 126,493

[22] Filed: Mar. 3, 1980

Related U.S. Application Data

[62] Division of Ser. No. 54,720, Jul. 5, 1979, Pat. No. 4,225,507.

[51] Int. Cl.$^3$ .................. C07C 143/75; C07C 143/79
[52] U.S. Cl. ...................................... 560/12; 562/430; 564/91; 564/98; 564/95
[58] Field of Search ................. 260/556 AC; 560/121, 560/10, 12; 562/427, 430

[56] References Cited

U.S. PATENT DOCUMENTS

| | | | |
|---|---|---|---|
| Re. 30,287 | 5/1980 | Marx et al. | 560/121 X |
| 3,954,741 | 5/1976 | Schaaf et al. | 260/557 R X |
| 4,158,667 | 6/1979 | Axen | 260/413 |
| 4,169,895 | 10/1979 | Hess et al. | 260/556 AC X |
| 4,191,694 | 3/1980 | Skuballa et al. | 260/556 AC X |

FOREIGN PATENT DOCUMENTS 2505519  8/1975  Fed. Rep. of Germany ........... 560/121

Primary Examiner—Thomas A. Waltz
Attorney, Agent, or Firm—Robert A. Armitage

[57] ABSTRACT

The present invention provides novel 19-hydroxy-19-methyl-6-oxo-PGF$_1$ sulfonylamides which are useful for pharmacological purposes, e.g., anti-asthmatic indications.

1 Claim, No Drawings

19-HYDROXY-19-METHYL-6-OXO-PGF$_1$ SULFONYLAMIDES

DESCRIPTION

CROSS REFERENCE TO RELATED APPLICATIONS

The present invention is a divisional application of U.S. Ser. No. 054,720, filed July 5, 1979, now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-19-methyl-6-oxo-PGF$_1$ sulfonylamides. The novel prostacyclin analogs are useful for pharmacological purposes, e.g., as anti-asthmatic agents. The preparation and use of these compounds is incorporated here by reference from United States Ser. No. 054,720, filed July 5, 1979, now U.S. Pat. No. 4,225,507.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

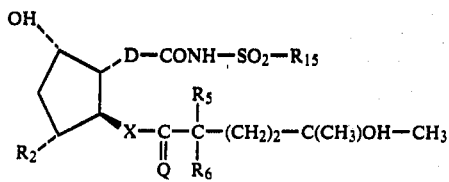

wherein D is —(CH$_1$)$_2$—CO—CH$_2$—L$_2$— or —CH$_2$—CO—CH$_2$—L$_3$—
wherein L$_2$ is
 (1) —(CH$_2$)$_j$—, wherein j is one to 4, inclusive,
 (2) —(CH$_2$)$_q$—CF$_2$—, wherein q is one, 2, or 3, or
 (3) —CH=CH—,
wherein L$_3$ is
 (1) —(CH$_2$)$_n$—, wherein n is one to 5, inclusive,
 (2) —(CH$_2$)$_p$—CF$_2$—, wherein p is 2, 3, or 4, or
 (3) —CH$_2$—CH=CH—;
wherein Q is oxo, α-H:β-H, α-OH:β-R$_4$, or α-R$_4$:β-OH, wherein R$_4$ is hydrogen or alkyl of one to 4 carbon atoms, inclusive,
wherein R$_2$ is hydrogen, hydroxyl, or hydroxymethyl;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein R$_{15}$ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive;
wherein X is
 (1) trans-CH=CH—,
 (2) cis-CH=CH—,
 (3) —C≡C—, or
 (4) —CH$_2$CH$_2$—,

I claim:
1. A prostacyclin-type compound of the formula

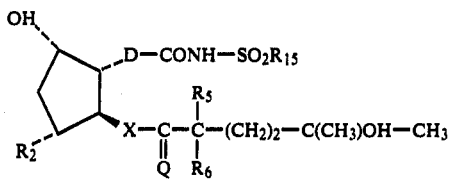

wherein D is —(CH$_1$)$_2$—CO—CH$_2$—L$_2$— or —CH$_2$—CO—CH$_2$—L$_3$—
wherein L$_2$ is
 (1) —(CH$_2$)$_j$—, wherein j is one to 4, inclusive,
 (2) —(CH$_2$)$_q$—CF$_2$—, wherein q is one, 2, or 3, or
 (3) —CH=CH—,
wherein L$_3$ is
 (1) —(CH$_2$)$_n$—, wherein n is one to 5, inclusive,
 (2) —(CH$_2$)$_p$—CF$_2$—, wherein p is 2, 3, or 4, or
 (3) —CH$_2$—CH=CH—;
wherein Q is oxo, α-H:β-H, α-OH:β-R$_4$, or α-R$_4$:β-OH, wherein R$_4$ is hydrogen or alkyl of one to 4 carbon atoms, inclusive,
wherein R$_2$ is hydrogen, hydroxyl, or hydroxymethyl;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein R$_{15}$ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive;
wherein X is
 (1) trans-CH=CH—,
 (2) cis-CH=CH—,
 (3) —C≡C—, or
 (4) —CH$_2$CH$_2$—.

* * * * *

UNITED STATES PATENT OFFICE
CERTIFICATE OF CORRECTION

Patent No. 4,267,352  Dated  12 May 1981

Inventor(s)  John C. Sih

It is certified that error appears in the above-identified patent and that said Letters Patent are hereby corrected as shown below:

Column 1, line 53, and Column 2, line 32,
"wherein D is $-(CH_1)_2-CO-CH_2-L_2-$" should read -- wherein D is $-(CH_2)_2-CO-CH_2-L_2-$ --.

Signed and Sealed this

Eighth Day of September 1981

[SEAL]

Attest:

GERALD J. MOSSINGHOFF

Attesting Officer

Commissioner of Patents and Trademarks